United States Patent [19]

Abdurakhmanov et al.

[11] 4,359,587

[45] Nov. 16, 1982

[54] METHOD FOR PREPARING CARBONYL COMPOUNDS

[76] Inventors: Mirkhasil Abdurakhmanov, proezd Morozova, 10, kv. 16; Rakhmatzhan K. Karimov, kvartal TS-27, 12, kv. 18, both of Tashkent, U.S.S.R.

[21] Appl. No.: 197,710

[22] Filed: Oct. 16, 1980

[51] Int. Cl.$^3$ .............................................. C07C 45/39
[52] U.S. Cl. .................................. 568/402; 568/473; 252/454
[58] Field of Search ................................ 568/402, 473

[56] References Cited

U.S. PATENT DOCUMENTS

| | | | |
|---|---|---|---|
| 2,170,855 | 8/1939 | Chitwood | 568/402 |
| 2,465,498 | 5/1945 | Uhl et al. | 568/473 |
| 3,156,735 | 11/1964 | Armstrong | 568/402 |
| 4,010,208 | 3/1977 | Aicher et al. | 568/473 |
| 4,208,353 | 6/1980 | Webster et al. | 568/473 |

OTHER PUBLICATIONS

Belousova et al., Zh. Prikt Khim, 1978, pp. 1560–1562.
Belousova et al., Chem. Abst., vol. 89, #179,466a, (1978).

Primary Examiner—James H. Reamer
Attorney, Agent, or Firm—Lilling & Greenspan

[57] ABSTRACT

The method for preparing carbonyl compounds according to the present invention comprises a vapor phase oxidizing dehydrogenation of $C_1$–$C_4$ alcohols at a temperature ranging from 500° to 700° C. in the presence of a silver catalyst, wherein silver is supported on a carrier having a crystalline structure incorporating alumina and silica in the form of cristobalite.

2 Claims, No Drawings

METHOD FOR PREPARING CARBONYL COMPOUNDS

The present invention relates to the organic synthesis and, more specifically, to a method for preparing carbonyl compounds by a vapor-phase oxidizing dehydrogenation of $C_1$-$C_4$ alcohols.

FIELD OF THE INVENTION

Among the carbonyl compounds extensively employed in industry formaldehyde is an important and valuable stock for the production of polyformaldehyde and various polycondensation resins constituting the foundation of the plastics industry. It is also employed in numerous organic synthesis processes and in the leather industry as a disinfectant and deodorizing agent in leather tanning processes. Formaldehyde is also useful in the production of a wide range of compounds such as glycerol, acrolein, ethylene glycol, pentaerythritol, urotropin, dyestuffs and pharmaceutical preparations. In recent years formaldehyde has found wide application in the production of isoprene and butadiene-important monomers in the synthetic rubber industry. Formaldehyde based resins are used in the synthetic fiber industry to produce nylon and kapron. Owing to its wide application in different branches of science and technology, the total world output of formaldehyde by 1980 has surpassed 12 million tons (as calculated for a 37%/by mass/aqueous solution of formaldehyde known as formalin).

Acetone and methyl ethyl ketone are employed mainly as solvents in the chemical, oil-refining and petrochemical industries, perfumes and manufacture of varnishes and paints.

BACKGROUND OF THE INVENTION

The vapor-phase oxidizing dehydrogenation of methanol to formaldehyde, of isopropanol to acetone and that of sec.butane to methylethylketone are among the most widespread industrial processes.

Known in the art are two basic industrial processes for the production of formaldehyde, namely:

1. Vapor-phase oxidizing dehydration of metahnol in a mixture with air oxygen and steam on a catalyst comprising pure silver or silver deposited onto a carrier.

The process is conducted at a temperature within the range of from 500° to 750° C. in an excess of methanol relative to its stoichiometric amount under partial oxidation conditions with the use of alcohol-air mixtures, wherein the concentration of methanol is above the upper limit of explosiveness (cf. J. F. Walker "Formaldehyde" Goskhimizdat Publishing House, 1957; British Pat. No. 1,131,380 published 1967).

2. Vapor-phase oxidation of methanol in a mixture with air oxygen on an oxidized iron-molybdenum catalyst. In certain cases the catalyst contains, as an additive, oxides of other metals. The process is conducted at a temperature within the range of from 370° to 430° C. in an excess of air relative to its stoichiometric amount under conditions of incomplete oxidation of methanol using alcohol-air mixtures with a content of methanol below the lower limit of explosiveness (cf. J. F. Walker "Formaldehyde" Goskhimizdat Publishing House, Moscow, 1957; British Pat. No. 1,131,380 published 1967).

The process for the production of formaldehyde on a silver catalyst occurs at higher space velocities of methanol supply. The existing production plants feature high productivity, and are simple and compact in size. For this reason, construction of such plants necessitates small initial investment per unit product, and enables production of both concentrated methanol-water solutions of formaldehyde and aqueous solution of formaldehyde without no methanol. At substantially identical production costs of the resulting formalin this process features greater flexibility, ease of control and replacement of the catalyst as compared to the processes contemplating the use of an oxidized iron-molybdenum catalyst.

However, this process provides an insufficient yield of the desired product and a low degree of conversion of methanol mainly due to low activity and selectivity of the catalysts employed which have a short service life and are difficult to regenerate or are not regenerable. Formalin produced with the use of such silver catalysts frequently has an increased content of formic acid which impairs its quality, and the purification of formalin from formic acid on a special ion exchange unit substantially increases production costs.

In the production of formaldehyde by an incomplete oxidation of methanol on oxidized iron-molybdenum catalysts there is observed a higher yield of the desired product at a substantially total conversion of methanol. The catalyst employed in this process has a longer service life and a low cost, however, it cannot be regenerated. Due to the necessity of supplying large quantities of excess air and a relatively low space velocity of methanol, as well as the use of condensation equipment and a tubular reactor with a complicated system cooling of the contact gases, the specific capital investments are increased, thereby increasing the production costs. For this reason, the method for preparing formaldehyde on silver catalysts is the most widespread in the industry because it is profitable on high-capacity units due to lower unit capital investments.

The principal process flow-sheet for the production of formalin by oxidizing dehydrogenation of methanol in a mixture with air oxygen and steam in the presence of silver catalysts is substantially the same in the majority of chemical plants. The units for the production of methanolic formalin (with a content of formaldehyde of from 37 to 44% by mass, methanol—5 to 12% by mass and formic acid—up to 0.04% by mass) incorporate, as a rule, apparatus for contact oxidizing dehydrogenation of methanol and absorption of formaldehyde and the unreacted methanol from the contact gases by means of water. To obtain methanolic formalin with an increased concentration of formaldehyde (up to 50-55% by mass) and a relatively low content of formic acid (below 0.04% by mass), the units can incorporate apparatus for concentrating of formalin and ion-exchange purifiers. In the production of methanol-free formalin (with a content of formaldehyde of up to 50-55%, methanol—up to 1.0% and formic acid up to 0.04% by mass) the process units, as a rule, incorporate all the above-mentioned apparatus. The recovered unreacted methanol from the crude formalin in a rectification column is recycled back to the process after purification.

The process of contact oxidizing dehydrogenation of methanol to formaldehyde on silver catalysts under commercial production conditions is generally conducted in the following manner.

Methanol is fed into a mixer, wherein it is diluted with steam condensate or water to a concentration of from 65 to 90% by mass. After the mixer the resulting aqueous-alcoholic mixture is delivered into an alcohol-evaporator, whereinto air is fed which is preliminarily cleaned to remove foreign matter, and compounds of sulphur and ammonia. In the alcohol evaporator vapors of methanol and water are formed at a temperature within the range of from 50° to 80° C. which are mixed with water. After the alcohol evaporator the alcohol-air mixture has the following approximate composition: methanol—36.2%, water—15.3%, oxygen—9.6% and nitrogen—38.9% is fed into an overheater. In the overheater the mixture is heated to a temperature of from 100° to 120° C. and the resulting alcohol-vapor-air mixture is fed into a contact apparatus having passed through a fire-retarder.

In the contact apparatus, on a silver catalyst and at a temperature of from 500° to 750° C., methanol is converted to formaldehyde which is in a mixture with the following by-products: $CO_2$, CO, $H_2$, $CH_4$ and HCOOH. The contact gases after the zone of contact with the catalyst are passed into the lower section of the contact apparatus to a subcontact cooler, wherein they are cooled to a temperature of from 70° to 150° C. Then the contact gases, while cooling in a heat-exchanger to a temperature not exceeding 20° C., are passed into an absorption column, wherein they are sprinkled with water. As a result of absorption of formaldehyde and the unreacted methanol with water there is obtained methanolic formalin in the column still with the required content of the main product. The absorption gases formed in the absorption column with a specific content of $CO_2$, $O_2$, CO, $H_2$, $CH_4$ and $N_2$ comprising a mixture of water insoluble products of side reactions of the oxidizing dehydrogenation of methanol to formaldehyde. Nitrogen and the unreacted air oxygen are combusted in a flare or vented to the atmosphere.

In the production of methanolic formalin with a low content of formic acid, the crude formalin at the outlet of the absorption column is delivered into an ion-exchange purification column, while in the production of methanol-free formalin with an increased concentration of formaldehyde and a lowered content of formic acid, the crude formalin after the absorption column is delivered into a rectification column or an evaporator and further into an ion-exchange purificaion column. The unreacted methanol distilled-off from the crude formalin in the rectification column is recycled back to the process.

The principal process scheme of the units for oxidizing dehydrogenation of isopropanol to acetone and sec.butanol to methyl ethyl ketone, and ethanol to acetaldehyde on silver catalysts is identical with the above-described flow-sheet of the production of formalin, except for individual process parameters and particularities associated with the recovery of the desired product.

Known in the art are processes for the production of formaldehyde by vapor-phase oxidizing dehydrogenation of methanol on the following kinds of silver catalysts:

(1) On a silver catalyst with the use of methanol instead of water to remove the heat evolved in the reaction. The process is designed for the production of formaldehyde in a yield of 91–92% as calculated for the reacted methanol and is carried out at a temperature within the range of from 500° to 550° C. The service life of the catalyst is extended from 60–90 days (in similar processes) up to 150–240 days. The process features a high content of methanol in formalin due to a low degree of conversion of methanol per run which does not exceed 70% by mass. The latter, in turn, explains a low yield of formaldehyde as calculated for the passed methanol which does not exceed 65% by mass.

(2) On a granulated silver catalyst at a temperature of 500° C. To increase the yield of formaldehyde and ensure a low content of by-products, conversion of methanol is maintained at the level of 60% by mass. The excess of methanol is distilled-off in a rectification column and recycled, after purification, back to the process. The desired product withdrawn from the column still comprises a 37–50% aqueous solution of formaldehyde containing no methanol.

The process features a low degree of conversion of methanol, a low specific output, as well as the necessity of using a rectification unit. The employed catalyst comprises pure silver, which is expensive and has a short service life not exceeding 90 days.

(3) On a catalyst containing silver on a supporting screen made of stainless steel or an alloy of copper with 0.1–0.6% by mass of arsenic. In the former case the yield of formaldehyde as calculated for the passed methanol is 73.5% by mass, conversion is as high as 83% by mass; the time of stable operation or, accordingly, the service life of the catalyst is about 21 days. In the former case the yield of formaldehyde is 76.5% by mass, the degree of conversion is 84% by mass; the time of stable operation is 98 days.

The process features low yields of the desired product, reduced service life of the catalyst and low conversion of the starting feedstock.

(4) On a catalyst comprising crystalline silver. There are developed two processes for the production of formaldehyde on this catalyst. The first process is conducted at a temperature of from 600° to 650° C., wherein the degree of conversion of methanol is 77 to 87% by mass. The unreacted methanol is recovered by distillation and recycled. The second process is conducted at a temperature of from 680° to 720° C. The degree of conversion of methanol is about 97–98% by mass. The yield of formaldehyde as calculated for the converted methanol (selectivity of the process) is 89–91% by mass and similar in both processes. However, in the production of formaldehyde on said catalyst by the first process higher capital investments and operation expenses are involved due to the necessity of using process units for the recovery of methanol and ion-exchange purification for the removal of formic acid.

Both processes feature high material expenses, in the use of pure silver as the catalyst, and selectivity of these processes is insufficient.

Also known are processes for the production of carbonyl compounds by vapor-phase oxidizing dehydrogenation of $C_1$–$C_4$ alcohols, in particular oxidizing dehydrogenation of methanol to formaldehyde, isopropanol to acetone, sec. butanol to methyl ethyl ketone and ethanol to acetaldehyde at a temperature within the range of from 500° to 750° C. in the presence of such supported silver catalysts as:

(5) "Silver-on-pumice" catalyst. The process features a relatively low yield of the desired product and insufficient conversion of the starting feedstock. The yield of carbonyl compounds as calculated for the passed alcohol does not exceed 76% by mass, the yield as calculated for the converted alcohol is not more than 92% by mass; the degree of conversion of the alcohol is 83% by mass. Due to low mechanical strength and wear-resistance of pumice, in the course of the production of carbonyl compounds there are observed considerable irreversible losses of silver which affects the catalyst service life which does not exceed 180 days. In this case the catalyst cannot be regenerated and after its use it is delivered to refining units for the recovery of silver. In the production of formalin there are frequently obtained aqueous solutions of formaldehyde with an increased content of formic acid (above 0.02% by mass) which impairs the quality of the final product, whereas the use of ion-exchange purification unit increases to the material costs of production.

(6) "Silver-on-alumina" catalyst. The catalyst comprises silver deposited onto alumina. The carrier can also incorporate, as an additive, oxides of alkali metals and rare-earth metals such as sodium, titanium, magnesium, zirconium, selenium and the like in an amount ranging from 0.5 to 5% by mass. However, due to a low selectivity of the process and the formation of considerable amounts of formic acid in the production of formaldehyde, this process has not been commercially implemented in the production of carbonyl compounds (cf. USSR Inventor's Certificate No. 106533, Cl. B 60 p 1/44, 1956).

(7) "Silver-on-carborundum" catalyst. The process for the production of methyl ethyl ketone by oxidizing dehydrogenation of sec.butanol in the presence of this catalyst features a relatively high selectivity (up to 98.5% by mass). In the oxidizing dehydrogenation of methanol to formaldehyde the process selectivity is at about the same level as in the case of the "silver-on-pumice" catalyst and equal to not more than 92% by mass. However, due to low degrees of the feedstock conversion, the yield of the target carbonyl compounds as calculated for the passed alcohol likewise in the process of preparation of formaldehyde and that of methyl ethyl ketone on this catalyst does not exceed 72.5% by mass. For these reasons, this process has also not acquired commercial implementation in the production of carbonyl compounds (cf. S. M. Lakiza et al. "Regeneration of Spent Silver Catalysts", Journal "Neftepererabotka i neftekhimija" ("Petroleum Refining and Petrochemistry"), 1974, No. 3).

Therefore, the above-described processes for the production of carbonyl compounds by a vapor-phase oxidizing dehydrogenation of $C_1$–$C_4$ alcohols in the presence of silver catalysts both of pure silver and supported by a carrier, feature a low yield of the desired product per pass, low selectivity of the process and a short service life of the catalysts employed, as well as insufficient productivity of the process and the necessity of using ion-exchange purification units which increases the production costs and complicates the process scheme.

SUMMARY OF THE INVENTION

It is an object of the present invention to improve the quality of the desired product simultaneously with increasing its yield and lowering material expenses for the process.

This object is accomplished by a method for preparing carbonyl compounds by way of a vapor-phase oxidizing dehydrogenation of $C_1$–$C_4$ alcohols at a temperature within the range of from 500° to 700° C. in the presence of a catalyst, wherein, according to the present invention, use is made of silver deposited onto a carrier comprising a crystalline structure containing alumina and silica in the form of cristobalite.

The method according to the present invention makes it possible to increase the degree of conversion of alcohols simultaneously with increasing yields of the desired product as calculated form both the passed and converted alcohol, improve quality of the resulting product and reduce the capital expenses for the process due to increased productivity of the process units and lowered rates of consumption of the feedstock per unit product output.

It is advisable to use a catalyst which contains metallic silver in an amount of from 30 to 40% by mass of the catalyst.

The use of the catalyst with such a content of silver makes it possible to reduce the running-in time of the unit during the start-up period, which contributes to a higher productivity of the process and a reduced yield of the under-grade product.

To improve the process selectivity, it is desirable to make use of a catalyst, wherein the carrier contains alumina and silica as cristobalite at the following proportions of the components, percent by mass:

alumina: 9.5 to 13.3
silica in the form of cristobalite: 86.7 to 90.5.

DETAILED DESCRIPTION OF THE INVENTION

A catalyst is charged into a contact apparatus. As the catalyst, use is made of silver supported on a carrier having a crystalline structure incorporating alumina and silica, the latter being in the form of cristobalite. Heating of the electric ignition of the contact apparatus is switched-on and, when the catalyst bed temperature reaches 100° to 320° C., the supply of an alcohol-air mixture is started. The mixture temperature is 110°–120° C. and the space velocity of the alcohol supply is within the range of from 6,000 to 25,000 $hr^{-1}$.

Depending on the kind of the carbonyl compound to be obtained, the alcohol-air mixtures can be: methanol-air, isopropanol-air, air with vapors of sec-butanol, or an ethanol-air mixture.

Due to the exothermal character of the process, the temperature in the reaction (contacting) zone increases very rapidly and attains a required value within the range of from 500° to 700° C. As the predetermined temperature is attained in the reaction zone, the external heat is switched-off and the process occurs autogenously.

The running in time of the unit (the time necessary to start operation under normal process parameters including the composition of absorption gases and quality of the desired product) with the use of the catalyst according to the present invention is reduced to 8–12 hours as compared to 48–72 hours in the case of prior art catalysts employed in the same process. This is due to the crystalline structure of the catalyst according to the present invention, in particular due to the presence of silica therein in the form of cristobalite.

In the case of formalin production, the contact gas effluent from the reactor is cooled in a sub-contact cooler to a temperature of from 70° to 170° C. and supplied into an absorption system for the absorption of formaldehyde with water. In absorption columns an aqueous solution of formaldehyde with a predetermined content of the main product is obtained by adjusting the amount of the spraying water.

To obtain acetone and methyl ethyl ketone, the contact gas effluent from the reactor is cooled in a cooler to a temperature of not more than 20° C. and fed into a reaction column.

The catalyst is prepared in the following manner.

Into an aqueous solution of silver nitrate with a concentration of from 40 to 45% by mass, an appropriate amount of granules of amorphous alumosilicate is added with a content of $Al_2O_3$ of from 9.5 to 13.3% by mass and $SiO_2$ content of from 86.7 to 90.5% by mass. During the first 10-15 minutes the impregnation of alumosilicate with the solution of silver nitrate is conducted at a temperature of from 50° to 60° C., then the mass is heated to a temperature of from 100° to 120° C., finally evaporated and dried to a dry bulky state.

The resulting catalyst has the following physicochemical characteristics:

| (1) content of silver | 30-40% by mass |
|---|---|
| (2) content of the carrier | 60-70% by mass |
| (3) Carrier composition, % by mass: | |
| content of silica as cristobalite | 86.7-90.5 |
| content of alumina | 9.5-13.3 |
| (4) granule size, mm | 2-5 |
| (5) bulk density, kg/l | 1.2-1.9 |
| (6) specific surface area, $m^2/g$ | 1.0-2.0 |
| (7) crushing strength, kg/granule | 10-30. |

Samples of the starting alumosilicates and the catalysts prepared therefrom are subjected to an X-ray phase analysis on a diffractometer of the type URS-50 IM with a copper anticathode at a voltage on the tube of 35 kV and current of 10 mA. The presence, in the X-ray graph, of intrinsic lines with interplanar distances of 2.36, 2.05, 1.45, 1.23 Å etc., points to the fact that the deposited silver is present in the catalyst as metal. It should be noted that, while the starting alumosilicates are amorphous relative to X-rays, that after deposition of silver thereonto and calcination, the alumosilicates pass into a X-ray crytalline structure. There is observed the growth of crystals of silica with the information of cristobalite which is proven by the appearance, in the diffractogram, of its intrinsic lines with interplanar distances of 4.14, 2.52, 1.64, 1.07, 1.04 Å, etc.

It follows from the foregoing, that the catalyst according to the present invention differs from the known ones in both its chemical composition and structure of the carrier crystals.

The method according to the present invention, as compared to the prior art, makes it possible to:

increase the desired product yield as calculated for the passed and converted alcohol, as well as to increase the degree of conversion of the latter;

increase productivity of the process units and lower the rate of consumption of the feedstock per unit of the final product output;

improve quality of the final product relative to the content of acids without resorting to the use of an ion-exchange purification unit;

reduce the running-in time of process units and reduce the yield of under-grade product during the start-up period;

prolong the duration of a stable opertion of process units and, hence, the service life of the catalyst; reduce the consumption rate of the catalysts and, hence, silver per unit of the product output.

These advantages of the method according to the present invention make is possible to reduce material expenses for the production and, eventually, ensure the manufacture of carbonyl compounds with a low production cost and high quality purity.

For a better understanding of the present invention, some specific Examples are given hereinbelow by way of illustration.

EXAMPLE 1

For the preparation of a catalyst, into a porcelain cup there are charged 47.3 of salt of silver nitrate, mixed with 70 ml of distilled water preheated to 60° C., and dissolved under agitation. Into the final solution there are charged 70 g of alumosilicate granules containing 9.5% by mass of $Al_2O_3$ and 90.5% by mass of $SiO_2$. During the first 10-15 minutes the impregnation occurs without heating, whereafter the mass is preheated to the solution reflux, evaporated under stirring and dried to a dry bulky state.

The resulting catalyst comprises silver (in the amount of 30% by mass) deposited onto a carrier having a crystalline structure containing $Al_2O_3$—9.5% by mass, $SiO_2$ as cristobalite—90.5% by mass. The catalyst is charged into a flow-type reactor. The reactor heat is switched-on and, when the temperature of 320° C. across the catalyst bed is reached, the supply of a methanol vapor-air mixture at a temperature of 120° C. and space velocity of the alcohol supply of 15,000 $hr^{-1}$ is started. The molar ratio between oxygen and methanol in the alcohol-air mixture is 0.35:1.0 respectively and the concentration of methanol in the supplied aqueous alcohol mixture is 70% by mass. The temperature in the reaction zone is maintained at 640° C. The contact gas ($CH_2O$, $CH_3OH$, $HCOOH$, $CO_2$, $CO$, $O_2$, $H_2$, $CH_4$ and $N_2$) effluent from the reactor is cooled in a sub-contact cooler to a temperature of 100° C. and delivered into an absorption system for absorption of formaldehyde with water.

Conversion of methanol reaches 85% mol., the yield of formaldehyde as calculated for the passed methanol is 78 mol.% that calculated for the converted methanol is 91 mol.%.

EXAMPLE 2

For the preparation of a catalyst, into a porcelain cup there are charged 60 g of salt of silver nitrate, mixed with 85 ml of distilled water preheated to a temperature of 60° C. and dissolved under stirring. Into the thus-prepared solution there are introduced 58 g of alumosilicate granules containing 13.3% by mass of $Al_2O_3$ and 86.7% by mass of $SiO_2$.

During the first 10-15 minutes the impregnation occurs without heating, then the mass is heated to the boiling point of the solution, finally evaporated under stirring and dried to a dry bulky (fluid) state.

The resulting catalyst comprises silver (in the amount of 40% by mass) supported on a carrier having a crystalline structure containing 13.3% by mass of $Al_2O_3$ and 86.7% by mass of $SiO_2$ in the form of cristobalite.

The thus-prepared catalyst is charged into a flow-type reactor. The reactor heat is switched-on and when a catalyst bed temperature of 250° C. is reached, the supply of a methanol-vapor-air mixture at a temperature of 150° C. and a space velocity of 18,000 $hr^{-1}$ is started. The molar ratio between oxygen and methanol in the alcohol-air mixture is 0.35:1.0 respectively, and the concentration of methanol in the supplied aqueous alcohol mixture is 70% by mass. The temperature in the reaction zone is maintained at 660° C. The contact gas effluent from the reactor is cooled in a sub-contact cooler to a temperature of 100° C. and delivered into an absorption system for absorption of formaldehyde with water.

The conversion of methanol is as high as 92 mol.%, the yield of formaldehyde as calculated for the passed methanol is 90 mol.%, that calculated for the converted methanol is 96 mol.%.

EXAMPLE 3

For the preparation of a catalyst, into a evaporation cup there are charged 30 kg of silver nitrate, mixed with 40 liters of water preheated to a temperature of 50°-60° C. and dissolved under stirring. Into the final solution there are charged 34 kg of alumosilicate granules containing 11% by mass of $Al_2O_3$ and 88.7% by mass of $SiO_2$. The process of impregnation of the carrier with the solution of silver nitrate is effected in a manner similar to that described in Example 1.

The resulting catalyst comprises silver (in an amount of 35% by mass) supported on a carrier having a crystalline structure and containing 11% by mass of $Al_2O_3$ and 88.7% by mass of $SiO_2$ in the form of cristobalite.

The process of oxidizing dehydrogenation of methanol to formaldehyde is carried out in a commercial plant with an annual capacity of 30,000 ton of methanolic formalin, incorporating no units of rectification and ion-exchange purification. Into a contact apparatus there is charged the catalyst prepared as described hereinabove and the process is conducted at a temperature of from 660° to 680° C. in the reaction zone and the space velocity of the supply is methanol of 12,000 $hr^{-1}$ in the gas phase. The concentration of methanol in the supplied aqueous alcohol mixture is 70-82% by mass, while the temperature of the contact gases at the outlet of the sub-contact cooler is 120° C.

Formalin discharged from the still of the absorption column has the following quality characteristics, % by mass:

content of $CH_2O$: 36.5-44.5
content of $CH_3OH$: 4-8
content of HCOOH: 0.005-0.015.

The absorption gases have the following composition, percent by volume: $CO_2$—2.8-3.8; $O_2$—up to 0.6; CO—0.5-1.5; $H_2$—19.5-23.5; $CH_4$—up to 0.5; $N_2$ being the balance.

Conversion of methanol reaches 85-93% by mass; the yield of formaldehyde per the passed methanol is 78-86% by mass; as calculated for the converted methanol it is 91-94% by mass.

The service life of the catalyst amounts to 600-900 days. If coked for technological reasons, the catalyst can be readily subjected to an oxidizing reactivation and then repeatedly used. The rate of the catalyst consumption per ton of formalin is 3.5 to 4.5 g, the rate of silver consumption is 1.2-1.5 g/t. The rate of methanol consumption per ton of the produced formalin having the above-mentioned characteristics is 515 to 530 kg.

EXAMPLE 4

In contrast to Example 2, the process is conducted in a plant with an annual capacity of 60,000 ton of methanol-free formalin incorporating no unit of ion-exchange purification. The flow-sheet of the plant incorporates a unit for rectification of methanol and concentration of formalin by evaporation. The distilled-off methanol from the rectification column is recycled to the process. The latter is conducted at a temperature of from 640° to 660° C. and at a space velocity of the supply of methanol in the gas phase is 25,000 $hr^{-1}$. The concentration of methanol is the supplied aqueous alcohol mixture is 75 to 90% by mass.

The formalin discharged from the reaction column still has the following characteristics, percent by mass:

content of $CH_2O$: 37-44
content of $CH_3OH$: 7-15
content of HCOOH: 0.008-0.02.

The absorption gases have the following composition, vol. percent: $CO_2$—2.8-4.0; CO—0.4-1.5; $O_2$—up to 0.6; $H_2$—18.5-24; $CH_4$—up to 0.4, $N_2$ being the balance.

The formalin withdrawn after the column rectification of methanol and concentration of crude formalin has the following characteristics:

content of $CH_2O$: 50-53
content of $CH_3OH$: up to 1.0
content of HCOOH: 0.02-0.04.

The conversion of methanol is 70 to 78%. The yield of formaldehyde as calculated for the passed methanol is 66-70% by mass, as calculated for the converted methanol the yield is 90-94% by mass.

The service life of the catalyst is equal to 600-900 days. The spent catalyst can be subjected to an oxidizing regeneration and repeatedly used in the process. The rate of consumption of the catalyst per ton of formalin is 3.5-4.5 g, that of silver is 1.2-1.5 g/ton. The rate of consumption of methanol per ton of the produced of methanol-free formalin having the above-specified characteristics is 450 to 480 kg.

EXAMPLE 5

The catalyst employed for the production of acetaldehyde from ethanol is prepared in a manner similar to that described in Example 2 hereinbefore. The catalyst comprises silver in an amount of 40% supported on a carrier having a crystalline structure containing 13.3% by mass of $Al_2O_3$ and 86.7% by mass of $SiO_2$ in the form of cristobalite.

The resulting catalyst is charged into a flow-type reactor. The reactor heat is switched-on and upon achieving a temperature of 250° C. across the catalyst bed, the supply of an ethanol-air-vapor mixture is started at a temperature of the mixture of 120° C. and a rate of supply, as calculated for the alcohol, of 9,000 $hr^{-1}$. The molar ratio between oxygen and ethanol in the alcohol-air mixture is 0.5:1.0, respectively and the concentration of ethanol in the supplied alcohol-water mixture is 70% by mass.

The temperature in the reaction zone is maintained at 640° C. The contact gas effluent from the reactor is cooled in a cooler to a temperature of 100° C., then condensed to recover acetaldehyde.

The degree of conversion of ethanol is 94 mol.%, the yield of acetaldehyde as calculated for the passed ethanol is 88 mol.%, that calculated for the converted ethanol is 94 mol.%.

EXAMPLE 6

The catalyst employed for the production of acetone from isopropanol is produced in a manner similar to that described in Example 1.

The catalyst comprises silver in an amount of 30% by mass deposited on a carrier having a crystalline structure containing 9.5% by mass of $Al_2O_3$ and 90.5% by mass of $SiO_2$ in the form of cristobalite.

The resulting catalyst is charged into a flow-type reactor. The reactor heat is switched-on and, when a temperature of 250° C. across the catalyst layer is reached, the supply of an isopropanol-vapor-air mixture at a temperature of 120° C. is started at the rate of 6,000 hr$^{-1}$ of the alcohol in the gas phase. The molar ratio between oxygen and isopropanol in the alcohol-air mixture is 0.5:1.0 and the concentration of isopropanol in the supplied alcohol-water mixture is 70% by mass. The process is conducted at a temperature of 540° C. in the reaction zone. The contact gas effluent from the reactor is cooled in a cooler to a temperature of 100° C., then concentrated and acetone is recovered.

The conversion of isopropanol is 88 mol.%, the yield of acetone as calculated for the passed isopropanol is 82 mol.%, that calculated for the converted isopropanol is 92 mol.%.

EXAMPLE 7

The catalyst employed for the preparation of acetone from isopropanol is produced following the procedure similar to that described in Example 2 hereinbefore.

The catalyst comprises silver in the amount of 40% by mass deposited onto a carrier having a crystalline structure containing 13.3% by mass of $Al_2O_3$ and 86.7% by mass of $SiO_2$ in the form of cristobalite.

The resulting catalyst is charged into a flow-type reactor. The reactor heat is switched-on and when the temperature across the catalyst bed is made equal to 320° C., the supply of an isopropanol-vapour-air mixture at a temperature of 100° C. is started at a space velocity of the alcohol supply of 6,500 hr$^{-1}$. The molar ratio of oxygen to isopropanol in the alcohol-air mixture is 0.5:1 respectively and the concentration of isopropanol in the supplied alcohol-water mixture is equal to 70% by mass.

The temperature in the reaction zone is maintained at 560° C. The contact gas effluent from the reactor is cooled in a cooler to a temperature of 100° C., then condensed to recover acetone.

The conversion of isopropanol is equal to 92 mol.%, the yield of acetone as calculated for the passed isopropanol is 88 mol.%, the yield of acetone calculated for the converted isopropanol is 95 mol.%.

EXAMPLE 8

The catalyst employed for the production of methyl ethyl ketone from sec.butanol is prepared following the procedure similar to that described in Example 1.

The catalyst comprises silver in an amount of 30% by mass deposited onto a carrier having a crystalline structure containing 9.5% by mass of $Al_2O_3$ and 90.5% by mass of $SiO_2$ in the form of cristobalite.

The resulting catalyst is charged into a flow-type reactor. The reactor heating is switched-on and when the temperature across the catalyst bed reaches 250° C., the supply of a mixture of sec.butanol, steam and air at a temperature of 120° C. is started at a space velocity of 5,200 hr$^{-1}$ relative to the alcohol. The molar ratio of oxygen to sec.butanol in the alcohol-air mixture is 0.5:1 respectively and the concentration of sec.butanol in the supplied alcohol-water mixture is 74% by mass.

The temperature in the reaction zone is maintained equal to 540° C. The contact gas effluent from the reactor is cooled in the cooler to a temperature of 100° C., then condensed and methyl ethyl ketone is recovered.

The conversion of sec.butanol is 86 mol.%, the yield of methyl ethyl ketone as calculated for the passed sec.butanol is 79 mol.% and as calculated for the converted alcohol—92 mol.%.

EXAMPLE 9

The catalyst employed for the production of methyl ethyl ketone from sec.butanol is prepared following the procedure similar to that described in Example 2.

The catalyst comprises silver in the amount of 10% by mass supported on a carrier having a crystalline structure containing 13.3% by mass of $Al_2O_3$ and 86.7% by mass of $SiO_2$ in the form of cristobalite.

The resulting catalyst is charged into a flow-type reactor. The reactor heating is switched-on and when the temperature across the catalyst bed reaches 320° C., the supply of a mixture of sec.butanol, steam and air at a temperature of 100° C. is started at a space velocity of of 5,600 hr$^{-1}$ as calculated for the alcohol. The molar ratio of oxygen to butanol in the alcohol-air mixture is equal to 0.5:1 respectively and the concentration of sec.butanol in the supplied alcohol-water mixture is 74% by mass.

The temperature in the reaction zone is kept equal to 560° C. The contact gas effluent from the reactor is cooled in a cooler to 100° C. and then condensed to recover methyl ethyl ketone.

The conversion of secondary butanol is equal to 90 mol.%, the yield of methyl ethyl ketone as calculated for the passed secondary butanol is 85 mol.%, the yield of methyl ethyl ketone calculated for the converted secondary butanol is 95 mol.%.

What is claimed is:

1. In a method for preparing carbonyl compounds by vapor-phase oxidizing dehydrogenation of $C_1$-$C_4$ alcohols at a temperature of from 500° to 700° C. in the presence of a catalyst, the improvement which comprises utilizing a catalyst consisting essentially of metallic silver in an amount varying from 30–40% by weight of the total catalyst, supported on a carrier consisting essentially of, in the following proportions, in % by weight:

alumina: 9.5 to 13.3
cristobalite: 86.7 to 90.5.

2. The method of claim 1, wherein said catalyst has an X-ray diffraction pattern of intrinsic lines with interplanar distances of 2.36, 2.05, 1.45, 1.23 Å and 4.14, 2.52, 1.64, 1.07 and 1.04 Å.

* * * * *